US006303138B1

United States Patent
Peterson et al.

(10) Patent No.: US 6,303,138 B1
(45) Date of Patent: Oct. 16, 2001

(54) ENDOTHELIN-BASED COMPOSITIONS FOR ENHANCING CONNECTIVE TISSUE REPAIR

(75) Inventors: Dale R. Peterson, Carmel; Nancy Nousek-Goebl, Fishers; Todd P. Glancy, Fairmount, all of IN (US)

(73) Assignee: DePuy Orthopaedics, Warsaw, IN (US)

( * ) Notice: Subject to any disclaimer, the term of this patent is extended or adjusted under 35 U.S.C. 154(b) by 0 days.

(21) Appl. No.: 09/398,494

(22) Filed: Sep. 17, 1999

(51) Int. Cl.$^7$ ................................................ A61F 2/00
(52) U.S. Cl. ..................... 424/426; 424/400; 424/422; 424/423; 424/424
(58) Field of Search ................................. 424/400, 422, 424/423, 424, 426

(56) References Cited

U.S. PATENT DOCUMENTS

| | | | |
|---|---|---|---|
| 5,041,138 | * | 8/1991 | Vacanti et al. . |
| 5,270,300 | * | 12/1993 | Hunziker . |
| 5,668,288 | | 9/1997 | Storey et al. ........................ 546/257 |
| 5,700,289 | * | 12/1997 | Breitbart et al. . |
| 5,702,716 | * | 12/1997 | Dunn et al. . |
| 5,906,934 | * | 5/1999 | Grande et al. . |

FOREIGN PATENT DOCUMENTS

| | | |
|---|---|---|
| 0 525 813 A1 | 2/1993 | (EP) . |
| 0 839 525 A1 | 5/1998 | (EP) . |
| 00307987 | 12/2000 | (EP) . |
| WO 97/38676 | 10/1997 | (WO) . |
| WO 98/47489 | 10/1998 | (WO) . |
| WO 99/24061 | 5/1999 | (WO) . |
| WO 99/55310 | 11/1999 | (WO) . |

OTHER PUBLICATIONS

Boskey, A.L. et al. (1996) "Dentin Sialoprotein, Bone Sialoprotein, and Osteoprotin Inhibit Hydroxyapatite Growth" *Journal of Dental Research* 75: Sepcial Issue Abstract 912.

Chen, Y. et al. (1992) "Calcium and Collagen Binding Properties of Osteopontin, Bone Sialoprotein, and Bone Acidic Glycoprotein–75 from Bone" *Journal of Biological Chemistry* 267(34): 24871–24878.

Cooper, L.F. et al. (1998) "Spatiotemporal Assessment of Fetal Bovine Osteoblast Culture Differentiation Indicates a Role for BSP in Promoting Differentiation" *Journal of Bone and Mineral Research* 13(4): 620–632.

Dreyfus, J. et al. (1998) "HB–GAM/Pleiotrophin but Not RIHB/Midkine Enhances Chondrogenesis in Micromass Culture" *Experimental Cell Research* 241: 171–180.

Gorski, J.P. et al. (1990) "Bone Acidic Glycoprotein–75 Is a Major Syntetic Product of Osteoblastic and Localized as 75–and/or 50 kDa Forms in Mineralized Phases of Bone and Growth Plate and in Serum" *Journal of Biological Chemistry* 265(25): 14956–14963.

Imai, S. et al. (1998) "Osteoblast Recruitment and Bone Formation Enhanced by Cell Matrix–associated Heparin–binding Growth–associated Molecule (HB–GAM)" *Journal of Cell Biology* 143(4): 1113–1128.

Rubanyi, G.M. and Polokoff, M.A. (1994) "Endothelins: Molecular Biology, Biochemistry, Pharmacology, Physiology, and Pathophysiology" *Pharmacological Reviews* 46(3): 368–369.

* cited by examiner

Primary Examiner—Thurman K. Page
Assistant Examiner—P. E. McQueeney
(74) Attorney, Agent, or Firm—Alice O. Martin; Barnes & Thornburg

(57) ABSTRACT

The present invention is directed to bioactive composition that induce the repair of damaged or diseased connective tissues upon contact of the damaged or diseased tissues with the composition in vivo. More particularly the present invention is directed to the use of a composition comprising an effective amount of endothelin to enhance the repair of damaged or diseased bone and cartilage tissues.

25 Claims, No Drawings

ENDOTHELIN-BASED COMPOSITIONS FOR ENHANCING CONNECTIVE TISSUE REPAIR

This invention relates to implantable biocompatible compositions that induce the repair of damaged or diseased bone, cartilage or other connective tissues upon contact of the damaged or diseased tissues with the composition in vivo. The invention also relates methods of inducing repair. More particularly the present invention is directed to the use of a composition comprising an effective amount of endothelin to induce repair of damaged or diseased bone and cartilage tissues.

BACKGROUND OF THE INVENTION

Currently, bone defects are typically repaired by autografts or banked bone. Autografts have a good ability to unify the bone, and physicians often prefer to use bone from sources such as the iliac crest. However, procedures using autografts suffer from several drawbacks. First, autografts require a separate harvest operation, resulting in increased operative time and the use of blood transfusions. Secondly, patients often lack adequate amounts of material for harvesting and often experience donation site morbidity. Implantation of banked bone does not require the harvest operation, but its bone healing capability is not as high as that of autografts. Therefore, it is undesirable to use banked bone in severe conditions such as nonunion.

Because of these drawbacks, researchers have searched for compositions and methods for promoting bone growth without necessitating the use of autografts or banked bones. One potential source for bone growth promoting factors is the extracellular matrices of healthy bone and cartilage tissues. Extracellular bone matrix contains predominantly mineral (hydroxyapatite) and an organic matrix, where the major component of the organic matrix is collagen type I. The remaining components of bone matrices include a number of less abundant non-collagenous proteins and growth factors. For example, since the mid-1960's the osteoinductive activity of both demineralized bone matrix (DBM) and bone morphogenetic protein (BMP) has been studied, e.g., Ijiri (1992). In addition to DBM and BMP, many compounds possess biological activity and find wide use in medical applications such as prosthetic devices, drugs, blood components, and the like.

Endothelins, are a class of 21-amino acid vasoactive peptides with intra chain disulfide bonds. The proteins were initially isolated and purified from conditioned medium of cultures of porcine aortic endothelial cells. Endothelins have subsequently been found to be produced by many cells, and their production modulated by systemic hormones and local factors (Rubanyi and Polokoff, 1994). Endothelin can be isolated from a wide variety of warm-blooded vertebrate tissue sources using standard extraction techniques known to those skilled in the art.

It has been reported that incubation of cell populations with the endothelial cell polypeptide endothelin-1 affects osteoblast growth and function. Accordingly, there has been speculation that these proteins as well as numerous other isolated compounds may play a role in bone and cartilage repair. However, in vitro results may vary due to a variety of factors, including cell type, cell density, cell isolation procedures, and type of growth medium. Therefore, while useful, in vitro studies are not always predictive of in vivo activity.

For example over the last two decades prostaglandins had been reported as both increasing bone resorption as well as increasing bone formation. Analysis of the literature references reporting the conflicting activities of prostaglandins reveals that almost all reports of bone resorption were performed in vitro and almost all the studies reporting bone formation were done in vivo (Mark and Miller, 1993). The studies of bone growth in vitro were performed with tissue/organ cultures of bone or relatively pure isolated bone cell populations. The apparent conflicting reports of the predominant skeletal affects of the prostaglandins can be explained on the basis of the limitations of the cell culture systems used to study those effects. Similarly, initial reports of TGF- activity based on cell culture assays failed to correlate with observed in vivo activities. Therefore, skilled artisans appreciate that in vitro activity does not always predict in vivo results.

What is needed are compositions shown to repair connective tissue in vivo.

SUMMARY OF THE INVENTION

In accordance with the present invention, compositions comprising endothelin are used to induce growth of bone or cartilage at an in vivo site in need of repair. The disclosed compositions are administered to a warm-blooded species, either by implanting or injecting the composition, for in vivo contact with the site in need of repair.

Another aspect of this invention is a method for inducing new bone or cartilage growth at a predetermined in vivo site of a vertebrate species comprising the steps of contacting the site with a composition comprising substantially purified endothelin, in an amount effective to induce endogenous tissue growth, and a pharmaceutically acceptable carrier. In a preferred embodiment, the composition is in liquid form and the site is contacted by injection of the composition. In another preferred embodiment, the carrier is a polymer matrix comprising a polymer selected from the group consisting of polyesters, ionomers, poly(amino acids), polyvinyl acetate, polyacrylates, polyorthoesters, polyanhydrides, collagens, fibrins, starches, alginate, and hyaluronic acid. Alternatively, the carrier may be a metal, glass, or mineral salt. Preferred mineral salts include tricalcium phosphate, hydroxyapatite, and gypsum.

Still another aspect of this invention is a method of treating a bone or cartilage pathogenic condition in a warm-blooded vertebrate by administering a composition systemically to the warm-blooded vertebrate, wherein the composition comprises substantially purified endothelin, in an amount effective to induce endogenous tissue growth, and a pharmaceutically acceptable carrier.

Additional features of the present invention will become apparent to those skilled in the art upon consideration of the following detailed description of embodiments including the best mode of carrying out the invention.

DETAILED DESCRIPTION OF THE PREFERRED EMBODIMENTS

The present invention is directed to compositions comprising endothelin in a substantially pure form, and the use of such compositions to enhance the repair of bone and cartilage defects in vivo. As used herein the term "endothelin" is intended to include any of the related family members of native endothelin proteins isolated from human or other warm-blooded vertebrates, naturally occurring isoforms of endothelin, recombinant protein produced from endothelin encoding nucleic acid sequences, and protein fragments/peptides of endothelin proteins. An endothelin gene is defined herein to include any nucleic acid sequence encoding for endothelin, including the native gene sequences isolated from human or other warm-blooded vertebrates, any nucleic acid sequence encoding active fragments of endothelin, or any recombinant derivative thereof. As used herein, the term "substantially pure" is intended to mean purified to at least 90% purity, and preferably to 95% purity, as determined by polyacrylamide gel electrophoresis or amino acid analysis. "Purity" refers to degree of absence of contaminants and the like.

The compositions of the present invention can be used in a method for inducing the repair of damaged or defective tissues of a warm-blooded vertebrate. More particularly, endothelin can be used to repair the tissues of orthopedic and non-orthopedic wound sites, including bone, cartilage, tendon, ligament, muscle, skin and other soft tissues. In an embodiment the compositions of the present invention are used to repair fractures effectively and fill or bridge bone defects including for example, craniofacial defects or periodontal defects, joint fractures, chondral defects, superficial chondral defects, full thickness defects, osteochondritis dissecans, minuscule tears, ligament tears, tendon tears, muscle lesions, myotendinitis junction lesions, skeletal reconstruction following secondary bone loss to infection or neoplasm, and the treatment of various bone or cartilaginous diseases such as osteoporosis.

Many compounds that have been isolated from connective tissues have been reported as having osteogenic properties based on the response of cells to those compounds in vitro. However, in vitro-established activities often fail to provide sufficient guidance for selecting compounds that will exhibit the desired in vivo bone and cartilage repair enhancing activity. Accordingly, the present invention uses an in vivo assay technique to identify bioactive agents that induce the repair of bone and cartilage tissues. Advantageously, the present in vivo assay avoids the use of delivery carriers, such as collagen, which are known to exhibit osteogenic properties themselves. This unique in vivo assay identifies compounds that enhance bone repair. More particularly, the in vivo assay described in Example 1 demonstrates that endothelin enhances the repair of bone in vivo.

Endothelin may enhance the repair of these tissues either directly or indirectly. For example, endothelin may increase new bone formation at a localized site by directly stimulating osteoblast activity (i.e. by enhancing matrix production or by recruiting additional osteoblast cells), by increasing angiogenesis, or by inhibiting osteoclast resorption. In addition, the compositions of the present invention may participate in the recruitment of bone progenitor cells or bioactive agents to the localized site either by selective binding of endothelin to the progenitor cells or the bioactive agent, or endothelin may participate in the recruitment of cells through chemotaxis. It is also anticipated that endothelin can be used in a wound repair context in combination with a carrier material such as a ceramic or polymer, including the use of proteins such as collagen as the carrier material. In addition endothelin can be combined with autologous cells (such as bone or cartilage progenitor cells) or autologous proteins (such as fibrin).

In an embodiment, the compositions of the present invention comprise a delivery vehicle and a bioactive mixture comprising an effective amount of a substantially pure endothelin. In another embodiment, the compositions of the present invention comprise a delivery vehicle and a bioactive mixture comprising an endothelin gene. Delivery vehicles suitable for use in delivering bioactive agents to bone and cartilage in vivo are well known to those skilled in the art. In an embodiment the delivery vehicle comprises a polymer matrix, and the polymer matrix is formed from one or more biocompatible polymers. As used herein, "biocompatible" means that the polymer is non-toxic, non-mutagenic, and elicits a minimal to moderate inflammatory reaction. Preferably the biocompatible polymer is also biodegradable and completely degrades in a controlled manner into non-toxic residues. In this embodiment, the polymer matrix serves as a delivery vehicle for the bioactive mixture, concentrating the bioactive agent at a localized site of administration and controlling the release of the bioactive composition. The controlled delivery and release of endothelin to localized bone and cartilage sites is based on the use of biodegradable, biocompatible polymers in combination with bioactive molecules to achieve both efficacious release of molecules and removal of the polymer from the treatment site within a physiologically useful time period.

A variety of polymers can be used to form the implant for the purposes of delivering bioactive molecules to a predetermined in vivo site, including polyesters, polyvinyl acetate, polyacrylates, polyorthoesters, polyhydroxyethylmethacrylate (polyhema) and polyanhydrides. One of the advantages of polyesters in such applications is that they are both biodegradable and biocompatible. Aliphatic polyesters have been widely used in the area of biomaterials for implantable drug delivery devices, sutures, and general tissues supports, after injury or surgery. The polyesters traditionally of greatest interest for localized delivery of biomaterials are derived from lactide, glycolide, and -caprolactone monomers, with a fairly broad range of degradation profiles accessible through various termonomer combinations. The ester linkages in these aliphatic polyesters are hydrolytically and/or enzymatically labile and render the polymers degradable in aqueous environments.

In a preferred embodiment, polymers such as polyanhydrides, polyester anhydrides, or ionomers are used. Alternatively, other polymers such as polylactic acid and polyorthoesters are also suitable. In an embodiment the polymer matrix comprises collagen fibers. Collagen has been reported to exhibit bioactive properties and enhances the repair of bone and cartilage tissues in vivo. Accordingly collagen fiber can function as both as a component of the delivery system as well as an active agent of the present bone and cartilage repair compositions. Other polymers suitable for use in forming the polymer matrix comprise fibrins, starches, alginate, and hyaluronic acid.

The composition of the polymer used to form the delivery vehicle matrix, as well as the molecular weight and physical properties of the polymer, can be varied according to the application. For example, hydrophobic polyanhydrides can be used where it is desirable to increase the time of degradation. Compounds can be mixed into, or polymerized with the polymer as required for additional strength or other desirable physical properties, using materials known to those skilled in the art from studies involving bone cements. For example, tricalcium phosphate or other ceramic type materials that provide better physical handling properties can be added to the composition.

In general, for repair of bone breaks, the polymer should release the material over a period of approximately 3 to 42 days (generally six weeks are required for sufficient repair to occur in humans before the bone is capable of bearing weight). The polymer should also degrade completely over a period no longer than about sixteen to twenty weeks. Release and degradation times will depend in part upon the polymer used and the bioactive materials to be released. In addition to polymers, various other time-release vehicles are known. An approach for parenteral administration employs the implantation of a slow-release or sustained-release system, such that a more or less constant rate of drug release is maintained. See, e.g., U.S. Pat. No. 3,710,795. Another approach is the use of an osmotic pump, as described in Example 1.

In accordance with an embodiment of the present invention, the delivery vehicle comprises polyester ionomers (salts of carboxy-terminated polyesters). The polyester ionomers exhibit good solubility even at higher molecular weights dictated by implant structural/functional requirements. The polyesters are prepared from and degrade into naturally occurring metabolites for enhanced biocompatibility. The polyester ionomers are prepared from the corresponding carboxy-terminated polyesters by neutralization or partial neutralization with biocompatible, pharmaceutically acceptable salt-forming bases. In an embodiment the delivery vehicle comprises biodegradable carboxy-terminated polyesters in combination with the corresponding ionomers. The physical properties of polyester ionomers can be controlled by the degree of neutralization of the corresponding carboxy-terminated polyesters and to some extent by selection of the neutralizing base. The polyester ionomers can be used alone or in combination with their carboxy-terminated polyester precursor for use in construction of a biocompatible delivery vehicle for tissue repair and/or prolonged release of biologically active compounds.

The use of polyester ionomers as delivery vehicles is described in U.S. Pat. No. 5,668,288, the disclosure of which is incorporated herein by reference. In general the polyester ionomers, is a divalent residue of a polyester. The polyester can comprise a homopolymer, copolymer, or terpolymer of biocompatible hydroxy acids, for example, lactic acid, glycolic acid, -hydroxy caproic acid, and -hydroxy valeric acid. Alternatively, the polyester can be formed using copolymerization of a polyhydric alcohol and a biocompatible polycarboxylic acid. Most typically such copolymers are formed between dihydric alcohols, for example, propylene glycol for biocompatibility and biocompatible dicarboxylic acids.

The bioactive component of the present compositions includes endothelin optionally combined with a pharmaceutically acceptable carrier, solubilizing agent, or filler material. To induce bone growth formation, endothelin should be administered at a concentration ranging from about 1 ng to about 500 $\mu$g/ml of the defect area. In one embodiment endothelin is administered in a concentration ranging from about 0.033 $\mu$g to about 330 $\mu$g/ml of the defect area. In addition, tricalcium phosphate, hydroxyapatite, gypsum, or other suitable physiological mineral sources can be combined with the compositions to assist in repair of damaged or diseased bone. In accordance with an embodiment, a physiological compatible mineral comprises up to 80% of the bioactive mix of the present composition. Alternatively, the physiological compatible mineral may comprises about 5% to about 50% of the bioactive mix, and more preferably comprises about 5% to 30% of the bioactive mix. In addition, the present compositions can be combined with known pharmaceuticals and bioactive agents to create a delivery system for the local treatment of bone disorders or diseases.

In addition, the bioactive component of the present compositions can be further combined with growth factors, growth factor binding proteins, or eukaryotic cells. Examples of suitable growth factors comprise: fibroblast growth factor, transforming growth factor (e.g., TGF- ), bone morphogenetic protein, epidermal growth factor, or platelet-derived growth factor. Examples of growth factor binding proteins are insulin-like growth factor binding proteins (IGFBP's) such as IGFBP 3 and 5. Examples of suitable eukaryotic cells comprise bone marrow cells, osteoblasts, and mesenchymal stem cells. The bioactive composition of the present invention can further include an osteogenic agent that stimulates or accelerates generation of bone upon implantation into a bone defect site. Examples of osteogenic agents comprise demineralized bone powder, morselized cancellous bone, aspirated bone marrow, bone or cartilage forming cells, and other bone sources.

The bioactive compositions of the present invention are useful for stimulating the growth of bone and cartilage tissues at a predetermined localized site in a warm-blooded vertebrate. The method comprises contacting the site in need of repair with a composition comprising substantially pure endothelin. In one embodiment the composition is surgically implanted at the site in need of repair and the composition comprises endothelin and a polymer matrix, wherein the polymer matrix controls the release of endothelin and concentrates endothelin at the desired site. Alternatively, the composition may be in an injectable form and the method of contacting the site in need of repair comprises injecting the composition into or adjacent to the site. The injectable form of the present composition typically comprises endothelin in combination with a pharmaceutically acceptable carrier. The viscosity of the compositions can be adjusted by controlling the water content of the compositions or the addition of pharmaceutically acceptable fillers or thickening agents known to those skilled in the art. In one embodiment, the injectable forms include collagen fibers and the viscosity of the composition is controlled by adjusting the pH of the composition to about 6.0 to about 7.5.

The compositions of the present invention can be combined with an effective amount of antibiotics, chemotherapeutic agents, additional growth factors, antigens, antibodies, enzymes, or hormones. For example, a composition comprising endothelin and an antibiotic may be useful in the treatment of osteomyelitis, thereby reducing the need for and risk of parenteral antibiotics. In addition, a composition comprising endothelin and an antineoplastic agent could be used for the local treatment of bone neoplasm and a composition comprising endothelin and an osteogenic or other growth factor (e.g., osteogenin, bone morphogenetic protein, parathyroid hormone, or TGF- ) could be used to accelerate the repair of skeletal defects as occurs with excessive trauma and with skeletal deficiency disorders such as osteogenesis imperfecta and osteoporosis.

As noted above the present compositions can be prepared in fluid forms for injection into a warm-blooded vertebrate. In an embodiment the injectable forms are used systemically to treat a warm-blooded vertebrate and provide therapeutic value for conditions such as osteoporosis, arthritis or other pathogenic situations that involve bone and/or cartilage. The injectable pharmaceutical formulation may be administered via the parenteral route, including subcutaneously, intraperitoneally, intramuscularly and intravenously. Examples of parenteral dosage forms include aqueous solutions of the active agent, in an isotonic saline, 5% glucose or other well-known pharmaceutically acceptable liquid carrier.

In an aspect of the present embodiment, the endothelin compound is dissolved in a saline solution containing 5% of dimethyl sulfoxide and 10% Cremphor EL (Sigma Chemical Company). Additional solubilizing agents are well-known to those familiar with the art and can be utilized as pharmaceutical excipients for delivery of the endothelin compounds. Other delivery vehicles are contemplated for use in accordance with the present invention and can be used to administer the fluid forms of the present invention systemically to a warm-blooded vertebrate. For example the delivery vehicle may be an oral dosage form, an epidermal patch or other delivery vehicle known to those skilled in the art.

EXAMPLE 1

Endothelin Enhances New Bone Formation in Vivo

A. In Vivo Testing of Endothelin Osteogenic Potential: The Rat Calvarial Defect Model To determine the osteogenic ability of endothelin, a well established model for measuring the in vivo induction of endogenous growth of bone tissue. In general the model involves the formation of circular defects (approximately 6–8mm in diameter) in the parietal bones of adult (greater than 6 months in age) Sprague Dawley rats. The defect is of a critical size such that the intraosseous wound would not heal by bone formation during the life of the animal.

The surgery was conducted with sterile technique, cap, mask, gown, and gloves. Animals were sedated with a cocktail of Ketoset 10 ml, with 0.15ml of 100mg/ml Xylazine and 0.3ml of 10mg/ml acepromarzine added, and the dosage was 0.1 ml/100g body weight. If additional sedation was needed Ketoset alone was used in 0.05 ml increments. After the rats were sedated, their heads were shaved from behind the ears to the tip of the nose and laterally, ventral to the ears. A three part scrub, alternating betadine and alcohol was performed. An ointment was placed in the eyes prior to scrubbing. After the animal surface was scrubbed, the animals were placed on V-trays with their heads positioned on a small stack of 4×4 gauze to make a level surgery site. The animals were immobilized by taping them to the tray using strips of tape running across the nose, ears, and back.

The tray with the immobilized animal was placed under a sterile drape on the surgery table. A skin incision was made in the midline of the skull, the periosteum was scraped off and retracted to expose the midline site. A 6 or 8mm trephine was used in a micro-drill under 40 pounds or less of pressure. Irrigation of the site while drilling was necessary to avoid thermal necrosis. As the bone was cut care was taken to avoid damage to the dura and sagittal sinus. The dura should be left intact if possible. If bleeding occurs the area was packed with gelfoam for a few minutes, then removed when bleeding stops. The defect edge was then scraped smooth.

A 6–8mm circle of gelfilm was placed between the brain and the composition comprising endothelin. After the composition was placed in the defect, the periosteal layer was sutured closed over the defect region using a 5–0 proline continuous suture pattern. The skin was closed with staples. Animals recovered in an incubator to avoid hypothermia, and after the animals were walking, they were returned to their cages.

B. Method of In Vivo Testing of Bioactive Compositions

In a novel modification of the rat calvarial defect model, the compositions of the present invention were administered directly to the localized in vivo defect site (the calvaria defect site in the rat calvaria defect model) of adult rats through the use of ALZET osmotic pumps. ALZET osmotic pumps (ALZA Scientific Products Palo Alto, Calif.) were implanted subcutaneously into Sprague Dawley rats in their backs, slightly posterior to the scapulae. The pumps were connected to a catheter wherein the catheter directs delivery of the pump's contents (endothelin) into the calvaria defect to provide a local dose of about 5 $\mu$g/ml of total defect volume.

The osmotic pumps were assembled prior to implantation. The pump assembly was first filled with the endothelin composition by attaching a syringe containing the solution to be delivered to the catheter tubing and filling the osmotic pump with the solution to be delivered. The filled osmotic pump is fitted onto its flow moderator. The pump assembly is then incubated in sterile saline (0.9%) at 37° C. for at least 4–6 hours. Optimal results are obtained by priming overnight. This step ensures that the osmotic pump is pumping continuously prior to implantation and minimizes the chance of clotting within the cannula or occlusion by tissue during delivery of the test agent. The assembly was then implanted into the host animal.

The rat was anesthetized and the pump apparatus was implanted into a subcutaneous pocket in the midscapular area of the back of the rat. To prepare the implantation site, the skin over the implantation site was shaved and washed, and a mid-scapular incision was made into the back of the animal. A hemostat was inserted into the incision and, by opening the jaws of the hemostat, the subcutaneous tissue was spread to create a pocket for the pump. The pocket should be large enough to allow some free movement of the pump (e.g. 1 cm longer than the pump). A filled pump was inserted into the pocket and connected to a catheter. The distal end of the catheter is placed into the calvaria defect for direct delivery of the endothelin composition to the defect. The pump insertion site was then closed with wound clips or sutures.

The manufacturer's guidelines were followed regarding the maximum drug delivery rates and durations utilized to minimize any nutrition-impairing stress or disruption of normal behavior. After its pumping lifetime has ended, the ALZET osmotic pump was removed.

Results

Experiments were conducted using an ALZET osmotic pump model 2002 which delivered its contents (200 $\mu$l volume) over a 14 day period to the defect site. The experiment was conducted over a total of 28 days after implantation of the pump. The rats were sacrificed at day 28 and a section through the center of the defect (extending from head to tail) was viewed histologically for bone growth. Two control animal groups were used, where the defect region received either saline only, or nothing at all (i.e. the pump was "empty"). The sections were scored in a blind manner for bone growth using a scale of 0–5 wherein the score is based on the amount of new bone growth observed in accordance with the following scale:

0 = no growth or resorption of existing bone;

1 = greater than zero to about 10% of the gap bridged with bone;

2 = about 10% to about 33% of the gap bridged with bone;

3 = about 33% to about 66% of the gap bridged with bone;

4 = about 66% or greater of the gap bridged with bone;

5 = complete bridging of the gap.

Table 1 describes analysis of in vivo bone growth response of rats to endothelin.

TABLE 1

Treatments and Histological Results in Rat Calvaria Defect Model

| Treatment | Concentration ($\mu$g/ml saline) | Dose ($\mu$g/ml defect) | Number of Animals | Average Score | Standard Deviation |
|---|---|---|---|---|---|
| Endothelin | 1.75 | 5.0 | 6 | 3.0 | 1.27 |
| Buffer Control | 0 | 0 | 28 | 2.5 | 1.23 |

In summary the introduction of recombinant human endothelin protein into a rat calvarial defect via the osmotic pump method enhances new bone formation. Furthermore, islands of cartilage were observed in some of the defects (in a model where cartilage does not normally form) thus suggesting that endothelin could be used to repair cartilage as well as bone.

EXAMPLE 2

Intravenous Infusion Via the External Jugular Vein

The endothelin compositions of the present invention can also be administered intravenously to provide systemic administration of the composition. Such systemic administration may provide therapeutic value for orthopedic conditions such as osteoporosis or other pathogenic conditions involving bone or cartilage. As described in Example 1, the ALZET pumps can deliver fluid compositions directly into the venous or arterial circulation via a catheter. ALZET pumps have been shown to pump successfully against arterial pressure with no reduction in flow. The following procedure details placement of a catheter in the external jugular vein. In many cases this site is preferable because of its size and ease of access, however, other sites may be used successfully.

An osmotic pump flow moderator is connected to one end of a catheter (inside diameter $\leq 0.030$ inches). The catheter should be 25% longer than the distance between the site of subcutaneous pump implantation (the midscapular region) and the site where the catheter enters the external jugular vein. The flow moderator and catheter is filled by attaching a syringe filled with endothelin composition to the free end of the catheter. The osmotic pump is filled with the endothelin composition and fitted onto the flow moderator. The syringe, which was used to fill the catheter, can now be detached and the flow moderator inserted until the white flange is flush with the surface of the pump. The pump and catheter should be completely filled and free of air bubbles. The filled pump and catheter are incubated in sterile saline (0.9%) at 37° C. for at least 4–6 hours. This step ensures that the osmotic pump is pumping continuously prior to implantation, minimizing the possibility of clotting and catheter occlusion during delivery of the test agent.

The complete assembly is then implanted into the animal as follows. The ventral portion of the animal's neck is shaved and cleaned and the neck is incised to one side of the midline, and the tissues spread along the head to tail axis. Using blunt dissection, the external jugular vein is located just beneath the skin and is elevated and cleaned for a distance of 1.5 cm. A silk ligature (3.0) is then placed around the head end of the cleaned vein and tied, and all large branches of the vein are tied off, but not cut. Two loose, overhand knots are placed at the heart end of the vein. Using the belly of sharp, curved iris scissors, the mid-portion of the vein is grasped, elevated and cut, so that an ellipsoidal piece of the vein wall is removed. (This technique is preferable to making a nick with the tip of the scissors.) The free end of the catheter is inserted into the hole in the vein wall, and advanced gently to the level of the heart (about 2 cm in an adult rat). The proximal (heart-end) ligatures are tied snugly around the catheter, being careful not to crimp the catheter. The distal (head-end) ligature is then tied around the catheter. The ends of all three ligatures are then cut off close to the knots.

A hemostat is then used to tunnel over the neck creating a pocket on the back of the animal in the midscapular region. The pump is positioned into this pocket, allowing the catheter to reach over the neck to the external jugular vein with sufficient slack to permit free head and neck movement. The incision in the skin of the neck is then closed with 2 or 3 wound clips or with sutures.

Although the invention has been described in detail with reference to preferred embodiments, variations and modifications exist within the scope and spirit of the invention as described and defined in the following claims.

DOCUMENTS CITED

Ijiri, S., Influence of Sterilization on Bone Morphogenetic Protein, Fourth World
Biomaterials Congress, April 24–28, (1992).
Rubanyi and Polokoff, Pharmacol. Rev. 46: 324–415 (1994).
Mark, S. and Miller, S. *Journal of Endocrinology*, Vol. 1 (1993).
U.S. Pat. No. 3,710,795
U.S. Pat. No. 5,668,288

We claim:

1. A composition for enhancing the growth of connective tissues, said composition comprising a delivery vehicle and an effective amount of substantially pure endothelin.

2. The composition of claim 1, wherein the connective tissue is bone.

3. The composition of claim 1, wherein the delivery vehicle comprises a polymer matrix formed from a biocompatible polymer.

4. The composition of claim 3, wherein the polymer matrix comprises a polymer selected from the group consisting of polyesters, ionomers, poly(amino acids), polyvinyl acetate, polyacrylates, polyorthoesters, polyanhydrides, collagens, fibrins, starches, alginate, and hyaluronic acid.

5. The composition of claim 1, further comprising a mineral salt selected from the group consisting essentially of tricalcium phosphate, hydroxyapatite, and gypsum.

6. The composition of claim 3, wherein the polymer matrix comprises a biodegradable polymer.

7. The composition of claim 6, wherein the biodegradable polymer is selected from the group consisting of collagens and polyester ionomers.

8. The composition of claim 1, further comprising additional growth factors, growth factor binding proteins, or eukaryotic cells.

9. A method for inducing endogenous growth of connective tissue at a an in vivo site in need of said growth, said method comprising:
   (a) obtaining a composition consisting essentially of isolated endothelin; and
   (b) administering an effective amount of the composition to the in vivo site.

10. The method of claim 9, wherein the isolated endothelin is combined with a biocompatible matrix to form an implantable composition.

11. The method of claim 9, wherein the connective tissue is bone.

12. A method for inducing localized connective tissue growth at a predetermined in vivo site of a vertebrate species, said method comprising
   contacting said site with a composition comprising substantially purified endothelin, in an amount effective to induce connective tissue growth, and a pharmaceutically acceptable carrier.

13. The method of claim 12, wherein the composition is in fluid form and the site is contacted by injection of the composition.

14. The method of claim 12, wherein the composition further comprises a biocompatible polymer matrix.

15. The method of claim 14, wherein the polymer matrix comprises a polymer selected from the group consisting of polyesters, ionomers, poly(amino acids), polyvinyl acetate, polyacrylates, polyorthoesters, polyanhydrides, collagens, fibrins, starches, alginate and hyaluronic acid.

16. The method of claim 12, wherein the pharmaceutically acceptable carrier comprises a mineral salt, or metal or glass compound.

17. The method of claim 16, wherein the mineral salt is selected from the group consisting essentially of tricalcium phosphate, hydroxyapatite and gypsum.

18. The method of claim 14, wherein the polymer matrix comprises a biodegradable polymer.

19. The method of claim 18, wherein the biodegradable polymer is selected from the group consisting of collagens and polyester ionomers.

20. The method of claim 14, wherein the composition is surgically implanted at the site.

21. The method of claim 12, wherein the composition is provided in a time-release delivery vehicle.

22. A method for treating a pathogenic condition in a connective tissue in a warm-blooded vertebrate, said method comprising administering a composition systemically to said warm-blooded vertebrate, wherein the composition comprises substantially purified endothelin, in an amount effective to induce endogenous connective tissue growth, and a pharmaceutically acceptable carrier.

23. The method of claim 22, wherein the composition is administered by parenteral injection.

24. The method of claim 22, wherein the connective tissue is bone.

25. The method of claim 24, wherein the pathogenic condition is osteoporosis.

* * * * *